United States Patent

An et al.

(10) Patent No.: US 6,326,513 B1
(45) Date of Patent: Dec. 4, 2001

(54) PROCESS FOR PRODUCING CREATINE OR CREATINE-MONOHYDRATE

(75) Inventors: Lihua An; Yuwen Zheng; Guoji Zhang, all of Tianjin (CN)

(73) Assignee: Tianjin Tiancheng Pharmaceutical Co., LTD, Tianjin (CN)

(*) Notice: Subject to any disclaimer, the term of this patent is extended or adjusted under 35 U.S.C. 154(b) by 0 days.

(21) Appl. No.: 09/648,631

(22) Filed: Aug. 28, 2000

(30) Foreign Application Priority Data

Sep. 7, 1999 (CN) .............................. 99118985 A

(51) Int. Cl.[7] .................................. C07C 241/00
(52) U.S. Cl. .............................................. 562/560
(58) Field of Search ................................ 562/560

(56) References Cited

U.S. PATENT DOCUMENTS 1,967,400 * 7/1934 Fischl .

5,719,319 * 2/1998 Weiss et al. .

OTHER PUBLICATIONS

Allen et al. (1970). Reaction of amino acids with guanidinating agents. Canadian Journal of Biochemistry 48 (11), pp 1189–1190.*
Derwent abstract (Acc. No. 1966–14072F) of JP 64021232B. A–amino–w–guanidino–carboxylic acid.*

* cited by examiner

*Primary Examiner*—Paul J. Killos
*Assistant Examiner*—Mahreen Chaudhry
(74) *Attorney, Agent, or Firm*—Armstrong, Westarman, Hattori, McLeland & Naughton, LLP

(57) ABSTRACT

The present invention relates to a process for producing creatine or creatine-monohydrate, comprising the step of reacting N-methylglycine, sodium N-methylglycinate and/or potassium N-methylglycinate with S-methylisothiourea and/or S-methylisothiourea sulfate in water or in a mixture of water and an alcohol solvent under the temperature from 15° C. to 140° C. and a pH of 7–13. By using the process of the present invention creatine or creatine-monohydrate with a higher purity can be produced at a much lower cost.

13 Claims, No Drawings

PROCESS FOR PRODUCING CREATINE OR CREATINE-MONOHYDRATE

FIELD OF THE INVENTION

The present invention relates to a process for producing creatine or creatine-monohydrate.

BACKGROUND OF THE INVENTION

Creatine is present in vertebrate muscle tissues, which has the function of promoting muscle growth and building up health. Creatine can be used as a food additive, and formulations containing creatine have become an essential everyday food additive of sportsman in many countries of the world, especially in Europe and America. It also becomes more and more popular among sports enthusiasts. The need of creatine used as food additives in China is also increasing.

Conventionally, the preparation of creatine involves extraction from biological raw materials such as muscle scraps. However, such a method is not cost effective and the use of such a source is not very sanitary. Currently, creatine is mainly prepared by chemical synthesis, i.e. through reaction of cyanamide with N-methylglycine (sarcosine). However, N-methylglycine is a very expensive raw material, moreover, a satisfactory yield can not be achieved. Chinese Patent application CN 1140707A filed by the SKW Trestberg Corporation Ltd. discloses a process for preparing creatine or creatine-monohydrate, which is aimed to achieve a commercially acceptable yield and a higher purity. In this process, cyanamide is reacted with sodium N-methylglycinate or potassium N-methylglycinate in water or in a mixture of water and an organic solvent at a temperature of 20° C. to 150° C. and pH of 7 to 14. However, the cost by using this method is very high, furthermore, harmful impurities such as cyanide and/or ammonia may be present in the product. Briefly speaking, known method for preparation of creatine is not satisfactory.

SUMMARY OF THE INVENTION

It is an object of the present invention to provide a new process for producing creatine or creatine-monohydrate with a higher purity and at a lower cost, so as to overcome the problems of the prior art.

The present invention provides a method for preparing creatine or creatine-monohydrate, comprising the step of reacting N-methylglycine, sodium N-methylglycinate and/or potassium N-methylglycinate with S-methylisothiourea and/or S-methylisothiourea sulfate in water or in a mixture of water and an alcohol solvent under the temperature from 15° C. to 140° C. and a pH of 7–13.

Preferably, the creatine or creatine-monohydrate thus produced is purified by using an alkaline complexing agent.

In the method of the present invention, the reaction of N-methylglycine, sodium N-methylglycinate and/or potassium N-methylglycinate with S-methylisothiourea and/or S-methylisothiourea sulfate is preferably proceeded at a temperature of 30° C. to 80° C.

In the method of the present invention, the reaction is preferably carried out at a pH between 9 and 11. When sodium N-methylglycinate or potassium N-methylglycinate is used as the raw material, the pH of the reaction solution is preferably adjusted by using an inorganic acid, which is preferably sulfuric acid or hydrochloric acid. Alternatively, if N-methylglycine is used as the raw material, the pH of the reaction solution is preferably adjusted by using an inorganic alkali, which is preferably sodium hydroxide or potassium hydroxide.

The molar ratio of N-methylglycine, sodium N-methylglycinate or potassium N-methylglycinate to S-methylisothiourea is preferably 1:5 to 4:1. Alternatively, the molar ratio of N-methylglycine, sodium N-methylglycinate or potassium N-methylglycinate to S-methylisothiourea sulfate is preferably from 1:2.5 to 2:1. More preferably, the number of moles of N-methylglycine, sodium N-methylglycinate or potassium N-methylglycinate approximately equals to the number of moles of S-methylisothiourea or S-methylisothiourea sulfate, such as 1:1.25.

The sodium N-methylglycinate or potassium N-methylglycinate used in the present invention may be in an unprocessed aqueous solution with a concentration of 20–40% (w/w) and a purity of 85–92% (w/w).

In the present invention, S-methylisothiourea or S-methylisothiourea sulfate is used as raw materials, which is inexpensive and no harmful impurities such as cyanide or ammonia and the like will be produced.

The reaction of the present invention can be performed in water, or in a mixture of water and ethanol or methanol, which facilitates the control of the temperature.

Preferably, A hot vapor is fed into the reaction solution to facilitate the crystallization of the product. If this process is kept for 5–10 hours, the yield and the purity of the product could be enhanced.

Upon completion of the reaction, the product can be separated by centrifugation, extraction-filtration or the like. In order to enhance the purity of the product, the separated product may be subjected to treatment with water and 95% ethanol, such as washing with distilled water and 95% ethanol, respectively.

Addition of an alkaline complexing agent such as disodium ethylene diamine tetracetate (disodium EDTA) to the solution in the crystallization process of the product may play a very important role to enhance the purity of the product.

A conventional counter-flow drier or a contact drier can be used for drying the wet product, preferably under the condition of $\leq 40°$ C. and 20 millibar pressure in a vacuum drier. Then a creatine-monohydrate can be obtained. If the product is dehydrated at 60–80° C. under normal pressure or in vacuum, creatine can be obtained. There is substantially no loss of the product during this process.

Creatine or creatine-monohydrate with a yield of 65–80% (w/w) and a purity of 99–102% (based on analysis of high performance liquid chromatography, HPLC) can be prepared according to the present invention, even though a sodium N-methylglycinate or a potassium N-methylglycinate having a purity of only 85–92% are used as the raw material. The method of the present invention is applicable in production on an industrial scale.

The properties of the creatine or creatine-monohydrate prepared according to present invention are as follows:

(1) Physical appearance: white crystalline powder, odorless;

(2) 1% water solution: colorless, transparent;

(3) Weight loss in drying process (105° C.): 10.5–11.5%;

(4) Broiling assay performed by crucible method: $\leq 0.1$ (creatine is used as the standard);

(5) Content of sulfate: $\leq 0.1\%$ (creatine is used as the standard);

(6) Content of heavy metal: $\leq 10$ ppm (creatine is used as the standard);

(7) Content of creatine: 99–102% (creatine is used as the standard);

(8) Particle size: 40 mesh (95%) (creatine is used as the standard).

Advantages of the process of the present invention are as follows:

1. The process for producing creatine or creatine-monohydrate according to present invention does not use cyanamide as the raw material, thus does not produce harmful by-products such as cyanide and ammonia.

2. The average yield of creatine or creatine-monohydrate in the process of the present invention is 71.15%, which is higher than that of the process disclosed in CN 11407074, which is 66.65%.

3. The purity of the creatine prepared according to present invention is 99–102%.

4. The sources of N-methylglycine, sodium N-methglglycinate, potassium N-methylglycinate, methylisothiourea and methylisothiourea sulfate used as the main raw material are rich and abundant, thus the cost for producing creatine or creatine-monohydrate is very much reduced.

The invention will be explained in further detail with reference to the following examples:

EXAMPLE 1

To a 20% (w/w) unprocessed aqueous solution of 833.1 g (about 1.5 mol) of sodium N-methylglycinate, a concentrated hydrochloric acid was added under stirring and cooling in an ice-salt liquor or an ice-water bath to adjust pH to 9.5. The temperature was kept below 15° C. in this process. Under the condition that the internal temperature was kept at 35° C., 291.9 g (1.1 mol) of S-methylisothiourea sulfate was slowly added into the solution under stirring within about 60 minutes. Then the solution was stirred for another 10 minutes at the internal temperature below 35° C. Thereafter, stirring was stopped, and the internal temperature was kept at 32° C. Reaction was allowed to proceed for 6 hours. Then a hot vapor was fed into the reaction solution for 35 minutes. A crystal was precipitated. After staying for 7 hours, the solution was centrifuged. After the liquid was removed, it was washed with distilled water (100 ml each time) until the pH value of the filtrate becomes to ≦7.5. Then the product was washed once with 140 ml of 95% ethanol, and a crude product was obtained. 1500 ml of water was added to the crude product, and the mixture was heated to 45° C. under stirring. Then pH was adjusted to 7.0 with addition of 10% sulfuric acid. Thereafter, the temperature was raised to 80° C. Then 0.3 g of disodium EDTA was added thereto, and the temperature was raised to 90° C. After stirring for 15 minutes, the solution was filtered. The filtrate was cooled to 20° C., and a crystal was obtained. The crystalline product was recovered by centrifugation, washed with 30 ml of distilled water and with 40 ml of 95% ethanol, respectively, and dried in a vacuum drier at 40° C. under 20 millibar pressure. 1044 g of the product was obtained. The yield of creatine-monohydrate was 72.0% (S-methylisothiourea was used as the standard), and the content or purity (HPLC) was 99.3%. After dehydrated at 80° C., creatine was obtained. There was substantially no product loss in this process.

EXAMPLE 2

To a 22% (w/w) unprocessed aqueous solution of 6160 g (about 12.2 mol) sodium N-methylglycinate, 20% sulfuric acid was added under stirring and cooling in an ice-salt liquor bath to adjusting the pH to 9.8. The temperature was kept below 15° C. in this process. Under the condition that the internal temperature was kept at 40° C., 3052 g (11 mol) of S-methylisothiourea sulfate was slowly added into the solution under stirring within 100 minutes. Then the solution was further stirred for 15 minutes at an internal temperature not more than 40° C. Thereafter, a hot vapor was fed into the solution for 45 minutes, and a crystal was precipitated. After staying for 7 hours, the solution was centrifuged to remove the mother liquor, then was washed with distilled water several times (80 ml each time) until pH value becomes to ≦7.6. The product was washed once with 1100 ml of 95% ethanol to obtain a crude product. 1260 ml of water was added to the crude product, and the mixture was heated to 45° C. under stirring. Then pH was adjusted to 7.0 with addition of 10% sulfuric acid. Thereafter, the temperature was raised to 80° C. Then 0.5 g of disodium EDTA was added thereto, and the temperature was raised to 90° C. After stirring for 15 minutes, the solution was filtered. The filtrate was cooled to a temperature below 20° C., and a crystal was obtained. The crystalline product was recovered by centrifugation, washed once with 50 ml of distilled water and once with 70 ml of 95% ethanol, and dried in a vacuum drier at 40° C. under 20 millibar pressure. 1044 g of the product (S-methylisothiourea was used as the standard) was obtained. The yield of creatine-monohydrate was 70.3, and the content or purity (HPLC) was 99.4%. After dehydrated at 80° C., creatine was obtained. There was substantially no product loss in this process.

EXAMPLE 3

The process of Example 1 was carried out, except that 20% unprocessed aqueous solution of potassium N-methylglycinate was used to react with S-methylisothiourea sulfate. The yield was 73.3%, and the purity was 99.3%.

What is claimed is:

1. A process for producing creatine or creatine-monohydrate, consisting of the steps of reacting N-methylglycine, sodium N-methylglycinate and/or potassium N-methylglycinate with S-methylisothiourea and/or S-methylisothiourea sulfate in water or in a mixture of water and an alcohol solvent under the temperature of 30° C. to 140° C. and a pH of 7 to 13; and purifying creatine or creatine-monohydrate produced by using an alkaline complexing agent.

2. A process according to claim 1, wherein, the reaction is carried out at a temperature of 30° C. to 80° C.

3. A process according to claim 1, wherein, the reaction is carried out at a pH between 9 and 11.

4. A process according to claim 1, further comprising the step of adjusting the pH of the reaction solution by using an inorganic acid selected from sulfuric acid and hydrochloric acid, when sodium N-methylglycinate or potassium N-methylglycinate is used.

5. A process according to claim 1, further comprising the step of adjusting the pH of the reaction solution by using an inorganic alkali, selected from sodium hydroxide and potassium hydroxide, when N-methylglycine is used.

6. A process according to claim 1, wherein, the molar ratio of N-methylglycine, sodium N-methylglycinate or potassium N-methylglycinate to S-methylisothiourea is 1:5 to 4:1, or, the molar ratio of N-methylglycine, sodium N-methylglycinate or potassium N-methylglycinate to S-methylisothiourea sulfate is from 1:2.5 to 2:1.

7. A process according to claim 1, wherein, the sodium N-methylglycinate or potassium N-methylglycinate used in the reaction is in an unprocessed aqueous solution with a concentration of 20–40% (w/w) and a purity of 85–92% (w/w).

8. A process according to claim 1, further comprising the step of feeding a hot vapor into the reaction solution to facilitate the crystallization of the product.

9. A process according to claim 1, wherein, the reaction is performed in water, or in a mixture of water and ethanol or methanol.

10. A process according to claim 1, further comprising the step of separating the product of the reaction and washing the separated product with water and 95% ethanol.

11. A process according to claim 1, wherein, the alkaline complexing agent is disodium EDTA.

12. A process according to claim 1, further comprising the steps of allowing the formation of a crystal after reaction, and drying the crystal under the condition of $\leqq 40°$ C. and 20 millibar pressure to obtain the creatine-monohydrate.

13. A process according to claim 1, further comprising the steps of allowing the formation of a crystal after reaction, drying the crystal under the condition of $\leqq 40°$ C. and 20 millibar pressure to obtain the creatine-monohydrate, and dehydrating the creatine-monohydrate under 60–80° C. to obtain creatine.

* * * * *